(12) United States Patent
Patel et al.

(10) Patent No.: US 12,390,273 B2
(45) Date of Patent: Aug. 19, 2025

(54) SURFACE AND SUBSURFACE TUMOR MAPPING FOR COMPUTER-GUIDED LASER SURGERY

(71) Applicant: Duke University, Durham, NC (US)

(72) Inventors: Jigar Patel, Seattle, WA (US); Weston Ross, Durham, NC (US); Patrick Codd, Durham, NC (US)

(73) Assignee: Duke University, Durham, NC (US)

( * ) Notice: Subject to any disclaimer, the term of this patent is extended or adjusted under 35 U.S.C. 154(b) by 405 days.

(21) Appl. No.: 18/088,304

(22) Filed: Dec. 23, 2022

(65) Prior Publication Data

US 2023/0127514 A1 Apr. 27, 2023

Related U.S. Application Data

(63) Continuation of application No. PCT/US2021/039877, filed on Jun. 30, 2021.

(60) Provisional application No. 63/045,919, filed on Jun. 30, 2020.

(51) Int. Cl.
*A61B 18/20* (2006.01)
*A61B 18/00* (2006.01)
*A61B 34/10* (2016.01)

(52) U.S. Cl.
CPC .......... *A61B 18/203* (2013.01); *A61B 34/10* (2016.02); *A61B 2018/00404* (2013.01); *A61B 2018/00452* (2013.01); *A61B 2018/00696* (2013.01); *A61B 2018/00904* (2013.01); *A61B 2034/107* (2016.02)

(58) Field of Classification Search
CPC ................. A61B 18/203; A61B 34/10; A61B 2018/00404; A61B 2018/00452; A61B 2018/00696; A61B 2018/00904; A61B 2034/107; A61B 2018/0047; A61B 2018/00565; A61B 2018/00595; A61B 2018/00702; A61B 2018/00732; A61B 2018/00738; A61B 2018/00761; A61B 2018/20359; A61B 2090/061

See application file for complete search history.

(56) References Cited

U.S. PATENT DOCUMENTS

| 6,140,314 A | 10/2000 | Zeimer | |
|---|---|---|---|
| 2008/0058782 A1 | 3/2008 | Frangineas et al. | |
| 2009/0234237 A1* | 9/2009 | Ross | A61B 5/416 600/504 |
| 2013/0197473 A1* | 8/2013 | McMillan | A61B 5/01 604/501 |
| 2015/0305623 A1* | 10/2015 | Bredenkamp | A61B 5/4227 604/503 |

(Continued)

FOREIGN PATENT DOCUMENTS

| WO | 2013024478 A1 | 2/2013 |
|---|---|---|
| WO | 2019246580 A1 | 12/2019 |

*Primary Examiner* — Michael W Kahelin
*Assistant Examiner* — Sebastian X Lukjan
(74) *Attorney, Agent, or Firm* — Kory D. Christensen

(57) ABSTRACT

Disclosed are systems and techniques for providing laser treatment. For example, a vasculature structure associated with a tissue region can be determined. Based on the vasculature structure, one or more laser parameters for configuring a laser to deliver laser energy to at least one blood vessel within the tissue region can be determined. Laser energy can be delivered to the at least one blood vessel to halt blood flow to a targeted area within the tissue region.

20 Claims, 10 Drawing Sheets

(56) References Cited

U.S. PATENT DOCUMENTS

2016/0317226 A1\* 11/2016 Jagdeo .................. A61B 90/06

\* cited by examiner

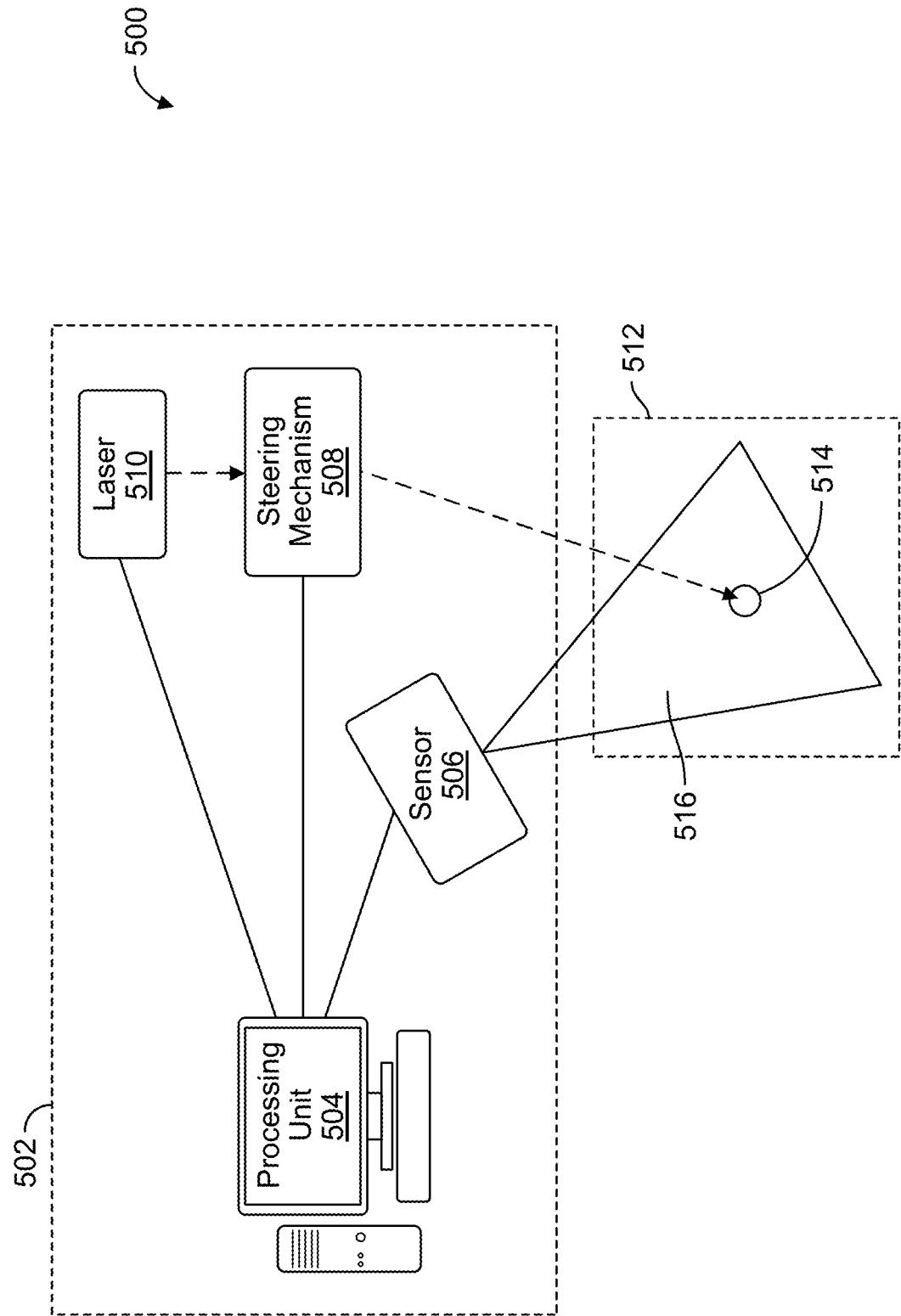

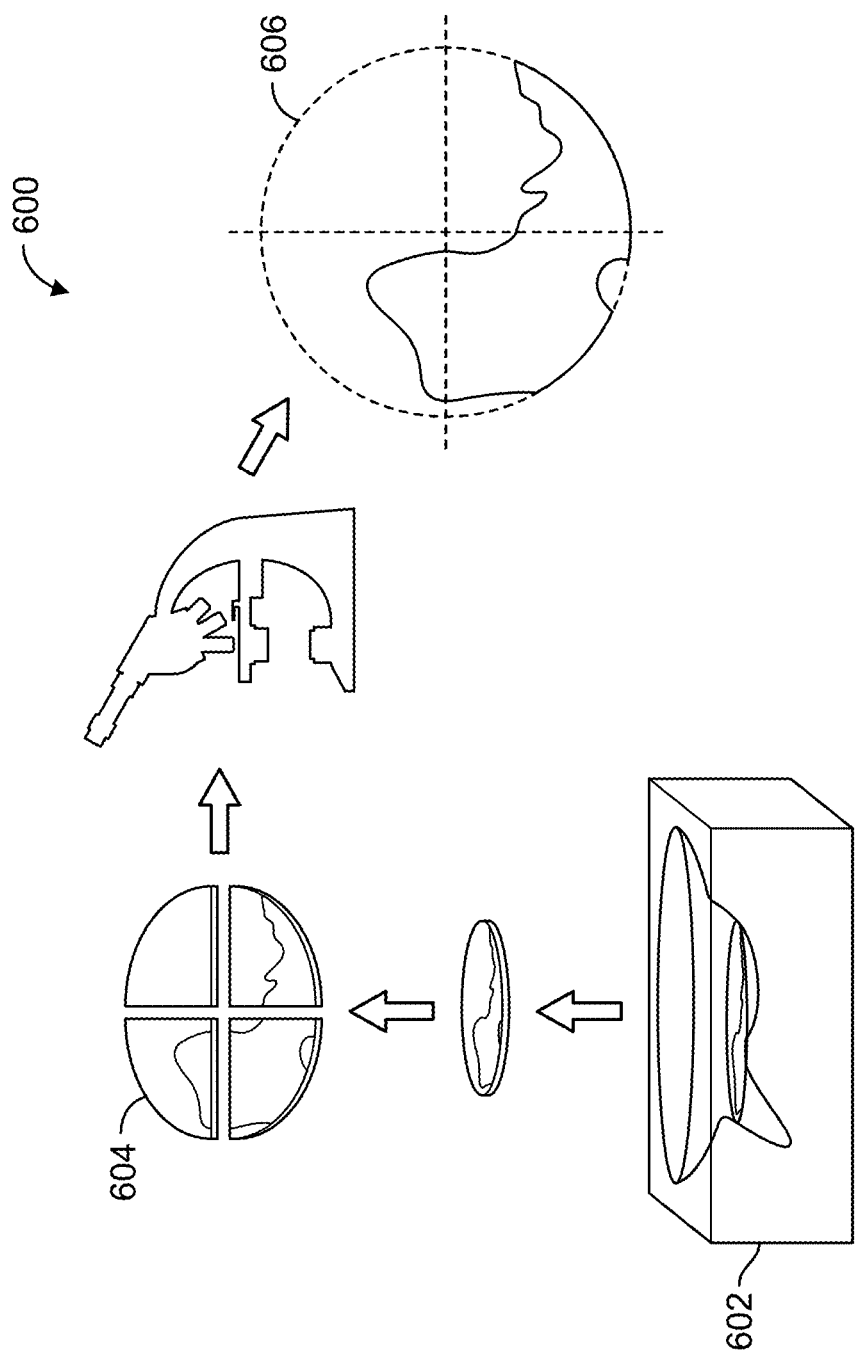

SURFACE AND SUBSURFACE TUMOR MAPPING FOR COMPUTER-GUIDED LASER SURGERY

CROSS-REFERENCE TO RELATED APPLICATIONS

This application is a continuation of PCT Application No. PCT/2021/039877, filed Jun. 30, 2021, for SURFACE AND SUBSURFACE TUMOR MAPPING FOR COMPUTER-GUIDED LASER SURGERY, which claims the benefit of U.S. Provisional Application No. 63/045,919, filed Jun. 30, 2020, both of which are incorporated herein by reference.

BACKGROUND

Laser-based devices are increasingly being employed across a wide range of cutaneous and subcutaneous applications including vascular and pigmented lesions, skin rejuvenation, and skin cancers among other elective and non-elective procedures. Basal cell carcinoma (BCC), squamous cell carcinoma (SCC), and early stage melanoma or melanoma in situ (MIS) are increasingly being treated with light-based devices. Although health outcomes continue to improve, some drawbacks remain. For example, in many cases treatment still relies on approaches that result in removal of, or damage to, a significant amount of healthy tissue. Thus, there is an ongoing need for improved methods to selectively remove unwanted tissue.

SUMMARY

The Summary is provided to introduce a selection of concepts that are further described below in the Detailed Description. This Summary is not intended to identify key or essential features of the claimed subject matter, nor is it intended to be used as an aid in limiting the scope of the claimed subject matter. One aspect of the present disclosure provides a method of laser treatment, the method includes: determining a vasculature structure associated with a tissue region; determining, based on the vasculature structure, one or more laser parameters for configuring a laser to deliver laser energy to at least one blood vessel within the tissue region; and delivering the laser energy to the at least one blood vessel to halt blood flow to a targeted area within the tissue region.

Another aspect of the present disclosure provides an apparatus for laser treatment. The apparatus comprises at least one memory, at least one laser, and at least one processor coupled to the at least one memory and the at least one laser. The at least one processor is configured to: determine a vasculature structure associated with a tissue region; determine, based on the vasculature structure, one or more laser parameters for configuring the at least one laser to deliver laser energy to at least one blood vessel within the tissue region; and deliver the laser energy to the at least one blood vessel to halt blood flow to a targeted area within the tissue region.

Another aspect of the present disclosure may include a non-transitory computer-readable storage medium having stored thereon instructions which, when executed by one or more processors, cause the one or more processors to: determine a vasculature structure associated with a tissue region; determine, based on the vasculature structure, one or more laser parameters for configuring a laser to deliver laser energy to at least one blood vessel within the tissue region; and configure the laser to deliver the laser energy to the at least one blood vessel to halt blood flow to a targeted area within the tissue region.

Another aspect of the present disclosure may include an apparatus for laser treatment. The apparatus includes: means for determining a vasculature structure associated with a tissue region; means for determining, based on the vasculature structure, one or more laser parameters for configuring a laser to deliver laser energy to at least one blood vessel within the tissue region; and means for delivering the laser energy to the at least one blood vessel to halt blood flow to a targeted area within the tissue region.

These and other aspects will be described more fully with reference to the Figures and Examples disclosed herein.

BRIEF DESCRIPTION OF THE DRAWINGS

The accompanying Figures and Examples are provided by way of illustration and not by way of limitation. The foregoing aspects and other features of the disclosure are explained in the following description, taken in connection with the accompanying example figures (also "FIG.") relating to one or more embodiments.

FIG. 5B is another block diagram of a laser treatment system.

FIG. 6 illustrates an example of a histological evaluation for determining a surface map to perform laser treatment.

DETAILED DESCRIPTION

Figure 1:
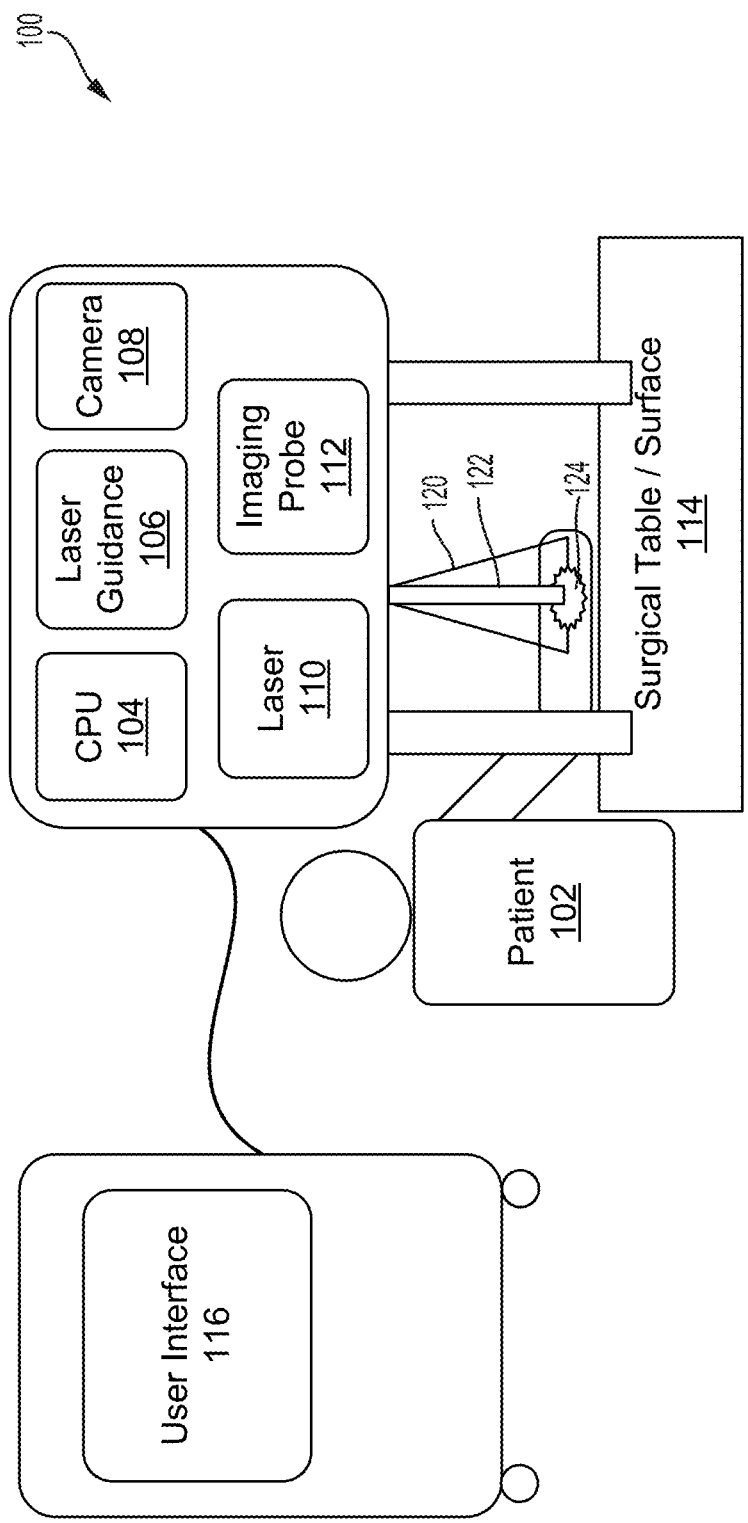
FIG. 1 is a block diagram of a laser treatment system.

For the purposes of promoting an understanding of the principles of the present disclosure, reference will now be made to preferred embodiments and specific language will be used to describe the same. It will nevertheless be understood that no limitation of the scope of the disclosure is thereby intended, such alteration and further modifications of the disclosure as illustrated herein, being contemplated as would normally occur to one skilled in the art to which the disclosure relates.

Articles "a" and "an" are used herein to refer to one or to more than one (i.e. at least one) of the grammatical object of the article. By way of example, "an element" means at least one element and can include more than one element.

"About" is used to provide flexibility to a numerical range endpoint by providing that a given value may be "slightly above" or "slightly below" the endpoint without affecting the desired result.

The use herein of the terms "including," "comprising," or "having," and variations thereof, is meant to encompass the elements listed thereafter and equivalents thereof as well as additional elements. As used herein, "and/or" refers to and encompasses any and all possible combinations of one or more of the associated listed items, as well as the lack of combinations where interpreted in the alternative ("or").

As used herein, the transitional phrase "consisting essentially of" (and grammatical variants) is to be interpreted as encompassing the recited materials or steps "and those that do not materially affect the basic and novel characteristic(s)" of the claimed invention. Thus, the term "consisting essentially of" as used herein should not be interpreted as equivalent to "comprising."

Moreover, the present disclosure also contemplates that in some embodiments, any feature or combination of features set forth herein can be excluded or omitted. To illustrate, if the specification states that a complex comprises components A, B and C, it is specifically intended that any of A, B or C, or a combination thereof, can be omitted and disclaimed singularly or in any combination.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure.

As used herein, "treatment," "therapy" and/or "therapy regimen" refer to the clinical intervention made in response to a disease, disorder or physiological condition manifested by a patient or to which a patient may be susceptible. The aim of treatment includes the alleviation or prevention of symptoms, slowing or stopping the progression or worsening of a disease, disorder, or condition and/or the remission of the disease, disorder or condition.

The term "effective amount" or "therapeutically effective amount" refers to an amount sufficient to effect beneficial or desirable biological and/or clinical results.

As used herein, the term "subject" and "patient" are used interchangeably herein and refer to both human and nonhuman animals. The term "nonhuman animals" of the disclosure includes all vertebrates, e.g., mammals and non-mammals, such as nonhuman primates, sheep, dog, cat, horse, cow, chickens, amphibians, reptiles, and the like.

Unless otherwise defined, all technical terms used herein have the same meaning as commonly understood by one of ordinary skill in the art to which this disclosure belongs.

Conventional treatment of skin lesions can include surgery and/or radiation therapy. However, such conventional treatment methods often cause collateral damage to healthy skin as well as patient discomfort. As a result, laser-based devices are increasingly being employed across a wide range of cutaneous applications including vascular and pigmented lesions, skin rejuvenation, and skin cancers among other elective and non-elective procedures. For example, basal cell carcinoma (BCC), squamous cell carcinoma (SCC), and early stage melanoma or melanoma in situ (MIS) are increasingly being treated with light-based devices.

Current methodologies for providing laser therapy utilize a hand-guided laser that delivers laser therapy to a circumscribed area defined by the shape of the laser spot and is sequentially repositioned to deliver treatment to the targeted area (e.g., the entire cancerous surgical site). Due to the geometric constraints imposed by the shape and size of the laser spot, which is commonly a fixed size square or circle, it is difficult to deliver uniform therapy to only the targeted area while minimizing collateral damage to surrounding healthy skin.

The present disclosure provides methods for improving laser-based treatments in dermatology. One aspect of the present disclosure provides a system that can be used to generate an image (e.g., three dimensional image) of a surgical site that can capture superficial and/or subsurface features in order to identify and/or delineate tissues of interest. For example, the image can be used to identify the vessel structure and/or histological information associated with the tissue of interest. In some examples, the image can be used to determine an optimized course of treatment, by which vessels are targeted with laser energy to "choke off" or otherwise effect the vessel in such a way that the downstream tissue is ultimately necrosed. In some embodiments, the present technology can be performed using either conventional or customized laser systems. For example, laser treatment can be performed using a computer-guided laser, an automated laser, a hand-guided laser, and/or any combination thereof.

FIG. 1 is a block diagram of a laser treatment system 100 according to one embodiment of the present disclosure. In some aspects, the laser treatment system 100 can be used to map surface and subsurface tumors of a patient 102 and to provide computer-guided laser treatment to patient 102. In some examples, the laser treatment system 100 can include a CPU 104 such as a microprocessor, although other types of controllers or processing devices may be used, such as a microcontroller, digital signal processor (DSP), application specific integrated circuit (ASIC), field-programmable gate array (FPGA) or like device. The CPU 104 may execute instructions stored in a memory (not illustrated), which may be implemented using any suitable non-transitory computer-readable medium, such as random access memory (RAM), read-only memory (ROM), electronically erasable programmable read-only memory (EEPROM), or the like. In some examples, the memory can also include non-volatile memory such as a hard disk drive (HDD), solid-state drive (SSD), and/or or optical storage unit, for long-term storage of data and/or application programs. In some cases, the CPU 104 can be coupled to (e.g., control and/or communicate with) one or more components in laser treatment system 100 (e.g., laser guidance 106, camera 108, laser 110, imaging probe 112, surgical table 114, and/or user interface F2).

In some examples, laser treatment system 100 can include imaging probe 112 (e.g., a sensor). In some cases, imaging probe 112 can be used to capture an image of a surgical site 124 on patient 102. For instance, imaging probe 112 can have a corresponding field of view 120 and imaging probe 112 can be used to capture a volumetric pre-treatment image of surgical site 124. In some aspects, imaging probe 112 can correspond to a dermatoscopic and/or a biomedical imaging technique such as photoacoustic imaging (PAI), optical coherence tomography (OCT), ultrasound, computed tomography (CT), magnetic resonance imaging (MRI), epiluminescence microscopy, any other imaging technique, and/or any combination thereof.

In some cases, laser treatment system 100 can include laser guidance 106 that can be used to control laser 110. For example, laser guidance 106 can correspond to a steerable mirror, a galvanometer, a robotic arm, any other component, and/or any combination thereof for positioning and aiming laser 110 to be incident on a desired point (e.g., surgical site 124). In some aspects, laser 110 can correspond to any type of laser device that can be configured to provide treatment to patient 102. For example, laser 110 can include carbon dioxide (CO2) lasers, neodymium-doped yttrium aluminium garnet (Nd:YAG) lasers, erbium-doped yttrium aluminium garnet (Er:YAG) lasers, argon-pumped tunable dye laser (APTDL), or any other type of laser. In some aspects, laser 110 can be associated with parameters such as wavelength, fluence, switched/non-switched, pulse width, spot size, power, etc. In some aspects, the emitted light 122 associated with laser 110 can have a fixed shape. In other embodiments, the emitted light 122 associated with laser 110 can be adjustable (e.g., adjusted with integrated optics). As illustrated, laser 110 can be used to deliver laser energy to surgical site 124, which corresponds to the arm of patient 102 that is rested on surgical table 114.

In some configurations, laser treatment system 100 can include a camera 108. In some examples, camera 108 can be used for detection and/or measurement of surgical site 124. In some aspects, camera 108 can correspond to a stereo vision system (e.g., a "depth" camera and/or a "color" camera) that can be used to capture three-dimensional colored images of surgical site 124. In some examples, the images captured by camera 108 can include topographical information that can be used to determine the distance to surgical site 124.

In some embodiments, laser treatment system 100 may further include a user interface 116. User interface 116 can include any input and/or output mechanism that enables user interaction with laser treatment system 100. For example, user interface 116 can include a microphone for speech, a touch-sensitive screen for gesture or graphical input, a keyboard, a mouse, speakers, motion input, speech and so forth. In some aspects, an operator can utilize the user interface 116 to review, modify, approve, and/or reject a treatment plan (e.g., laser parameters, surgical site 124, etc.). In some configurations, laser treatment system 100 may further include a network interface (not illustrated) for connecting to a computer network such as a local area network (LAN) and/or wide area network (WAN), including the Internet. Furthermore, one that is skilled in the art will recognized that the various components described above with respect to laser treatment system 100 may be implemented in separate devices, local or remote, that work in concert to perform the operations disclosed herein.

Figure 2:
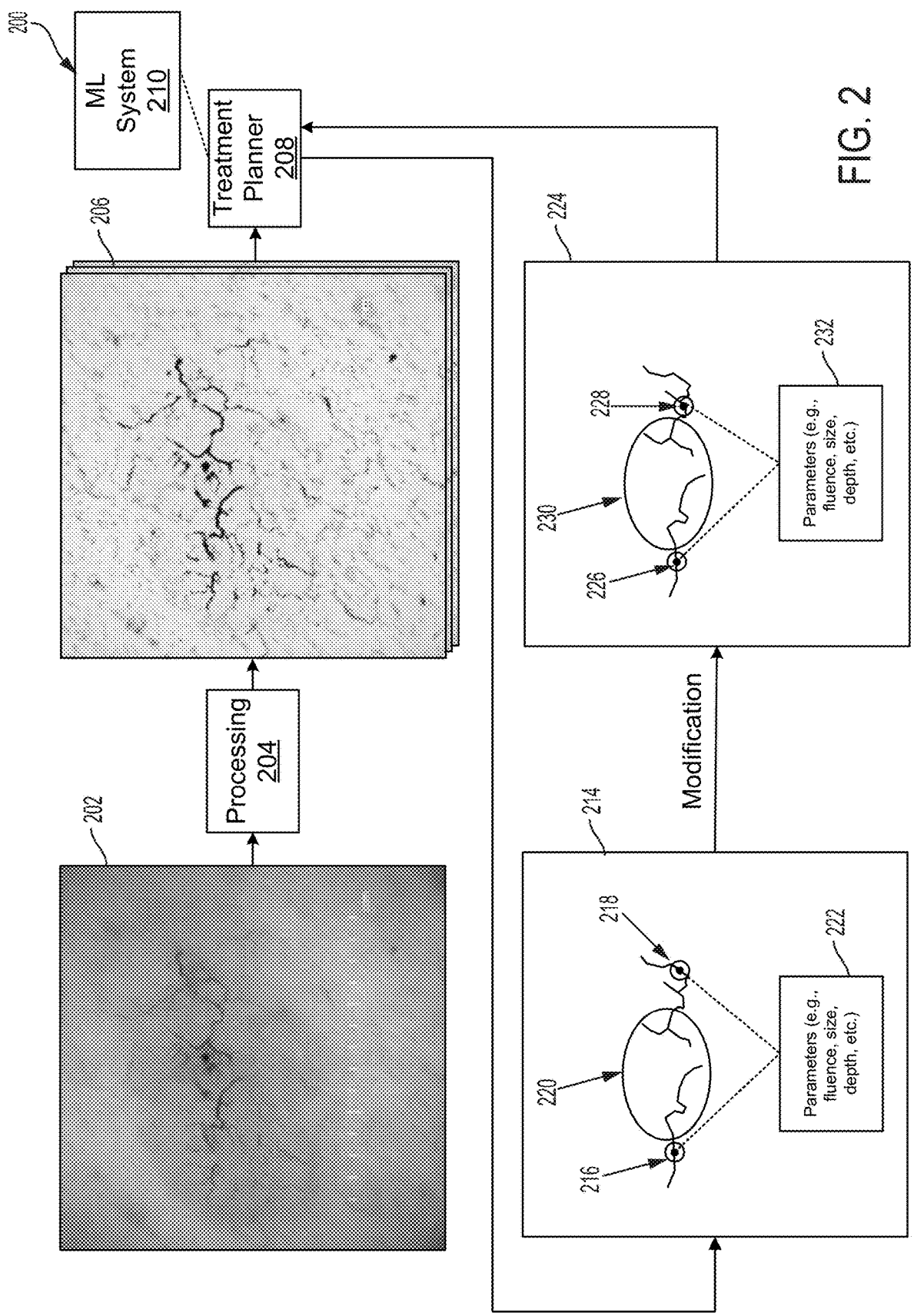
FIG. 2 is a flow diagram illustrating an example process for performing tumor mapping for computer-guided laser surgery.

FIG. 2 illustrates an example process 200 for performing tumor mapping for computer-guided laser surgery. In some aspects, the operations of process 200 can include obtaining an image 202 of a skin lesion. In some examples, image 202 can be obtained using dermatoscopy (e.g., epiluminescence microscopy) or any other suitable biomedical imaging technique (e.g., photoacoustic imaging (PAI), optical coherence tomography (OCT), ultrasound, computed tomography (CT), magnetic response imaging (MRI), etc.).

In some embodiments, image 202 can undergo processing 204 to yield a three-dimensional spatial map 206. In some examples, processing 204 of image 202 can include detecting, classifying, locating, mapping, and/or otherwise identifying the size (e.g., height, width, depth) of a region of interest and/or of a targeted area that may be within a region of interest. In some cases, processing 204 of image 202 can include determining a vasculature structure corresponding to a region of interest. For example, processing 204 can yield three-dimensional map 206 that can be used to locate and map spatial coordinates corresponding to the skin lesion. In one embodiment, the three-dimensional spatial map 206 can be used to determine the depth and diameter of subsurface peritumoral and intratumoral vasculature within a target lesion or generally skin vasculature.

In some aspects, the three-dimensional map 206 can be provided to a treatment planner 208 that can be used to generate a treatment plan. In some examples, treatment planner 208 can generate a treatment plan that includes one or more laser parameters such as power, fluence, spot size, pulse width, wavelength, any other laser parameter, and/or any combination thereof. In some cases, treatment planner 208 can also identify one or more targeted locations within a region of interest for delivering the laser energy. For instance, the treatment planner 208 can identify one or more blood vessels that deliver blood flow to a targeted area (e.g., a tumor). In some aspects, treatment planner 208 can determine a treatment plan that targets blood vessels such that delivery of laser energy enables selective photothermolysis, cauterization, and/or other effects in order to prevent or inhibit blood flow (e.g., "choke off") to a region of neoplasia or targeted dermal tissue. In some examples, a treatment plan can be implemented that can cause necrosis of a tumor or targeted tissue through vascular insufficiency.

In some embodiments, treatment planner 208 can be implemented with and/or otherwise include artificial intelligence algorithms such as machine learning system 210. In some examples, machine learning system 210 can include supervised machine learning techniques such as neural networks, linear and logistics regression, classification trees, support vector machine, any other suitable supervised machine learning technique, or any combination thereof. For example, a dataset that can include one or more laser parameters, vasculature structure, targeted tissue regions, and/or clinical outcomes (e.g., changes in targeted tissue region and/or changes in vasculature structure) can be selected for training ML system 210. In some aspects, a trained model in ML system 210 can be used to determine or modify a treatment plan.

In some examples, treatment planner 208 can generate a treatment plan that includes treatment plan 214. In some aspects, treatment plan 214 can identify one or more laser targets (e.g., target 216 and target 218) corresponding to locations in the vasculature structure associated with targeted area 220. In some cases, treatment plan 214 can include or be associated with one or more laser parameters 222 such as fluence, spot size, wavelength, depth, power, etc. In some embodiments, the one or more laser parameters 222 can be configured to target one or more blood vessels (e.g., based on vessel diameter and depth) in order to enable photothermolysis, cauterization, and/or otherwise inhibit blood flow to targeted area 220.

In some aspects, treatment plan 214 can be modified by treatment planner 208 (e.g., automatically, manually, via artificial intelligence, etc.) to yield treatment plan 224. For example, treatment planner 208 can determine (e.g., based on three-dimensional map 206) updates for one or more laser targets and/or one or more laser parameters. For example, treatment plan 224 includes target 226 and target 228 corresponding to locations in the vasculature structure associated with targeted area 230. As illustrated, target 228 in treatment plan 224 is shifted to a different location of a blood vessel as compared to target 218 in treatment plan 214. As noted with respect to treatment plan 214, treatment plan 224 can include one or more laser parameters 232 such as fluence, spot size, wavelength, depth, power, etc. In some examples, the one or more laser parameters 232 may be modified by treatment planner 208. In some embodiments, steps in process 200 such as imaging (e.g., obtaining image 202), processing 204, determining three-dimensional map 206, treatment planner 208, and/or modification of treatment plans can be performed sequentially, concurrently, or in a different order. For example, imaging can be repeated at the beginning, throughout, and/or at the end of a laser treatment procedure in order to capture an incrementally changing vascular map to further modify a treatment plan as necessary.

Figure 3:
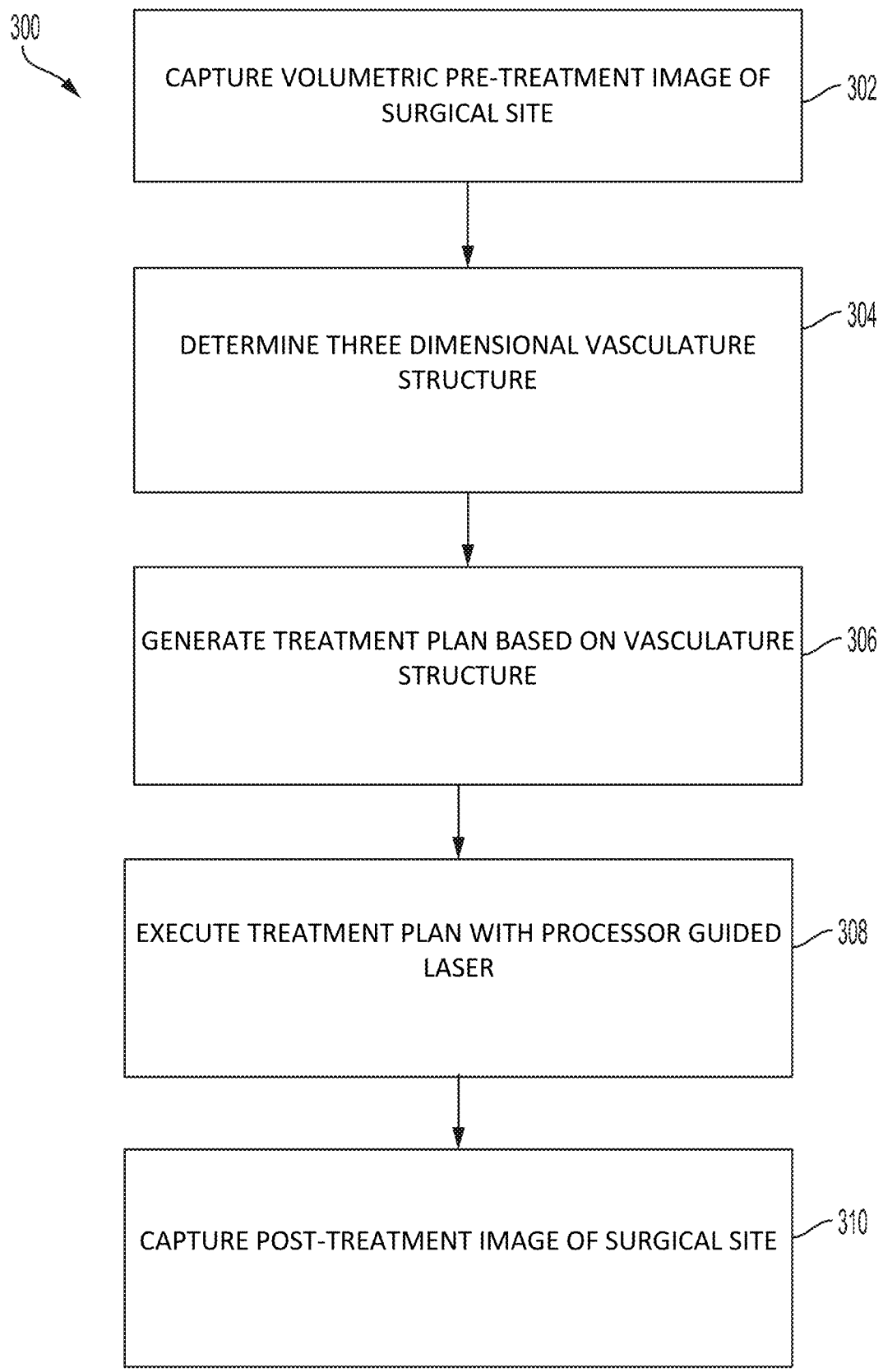
FIG. 3 is a flowchart illustrating an example method for performing imaging-based laser treatment.

FIG. 3 illustrates an example method 300 for performing imaging-based laser treatment. At block 302, the method 300 includes capturing a volumetric pre-treatment image of a surgical site. In some examples, the volumetric pre-treatment image can be captured using dermatoscopic (e.g. epiluminescence microscopy) or other biomedical imaging techniques (e.g. photoacoustic imaging (PAI), optical coherence tomography (OCT), ultrasound, computed tomography (CT), magnetic response imaging (MRI), and/or some other imaging technique. In some aspects, the pre-treatment image can capture both superficial and subsurface features associated with the surgical site.

At block 304, the method 300 includes determining a three-dimensional vasculature structure. In some examples, the three-dimensional vasculature structure can be determined based on the volumetric pre-treatment image. In some embodiments, the three-dimensional vasculature structure includes a map of one or more blood vessels that provide blood flow to a targeted tissue region. For instance, the three-dimensional vasculature structure can delineate tissues of interest and can include the corresponding vessel structure and/or histological information.

At block 306, the method 300 includes generating a treatment plan that is based on the vasculature structure. In some aspects, the treatment plan can identify one or more laser targets corresponding to locations in the vasculature structure associated with a targeted area within the surgical site. In some cases, the treatment plan can include or be associated with one or more laser parameters such as fluence, spot size, wavelength, depth, power, etc.

At block 308, the method 300 includes executing the treatment plan with a processor guided laser. In some examples, executing the treatment plan includes delivering laser energy (e.g., using the one or more laser parameters) to a targeted area at the surgical site. In some aspects, a computer-guided laser can include providing instruction to an operator for manual aiming of the laser. In further embodiments, a computer-guided laser can include direct guidance of the laser with a laser-guiding system such as a steerable mirror, galvanometer, robotic arm, or any other component and/or system that can be used to position the laser to be incident on the surgical site at a desired target as identified by the treatment plan.

At block 310, the method 300 includes capturing post-treatment image of the surgical site. In some aspects, the post-treatment image can be captured using one or more of the methods described with respect to the pre-treatment image at block 302. In some examples, the post-treatment image can be used to confirm that the laser treatment was successful. In some embodiments, the post-treatment image can be used to derive a post-treatment vascular map that can be used to update or modify the treatment plan.

Figure 4:
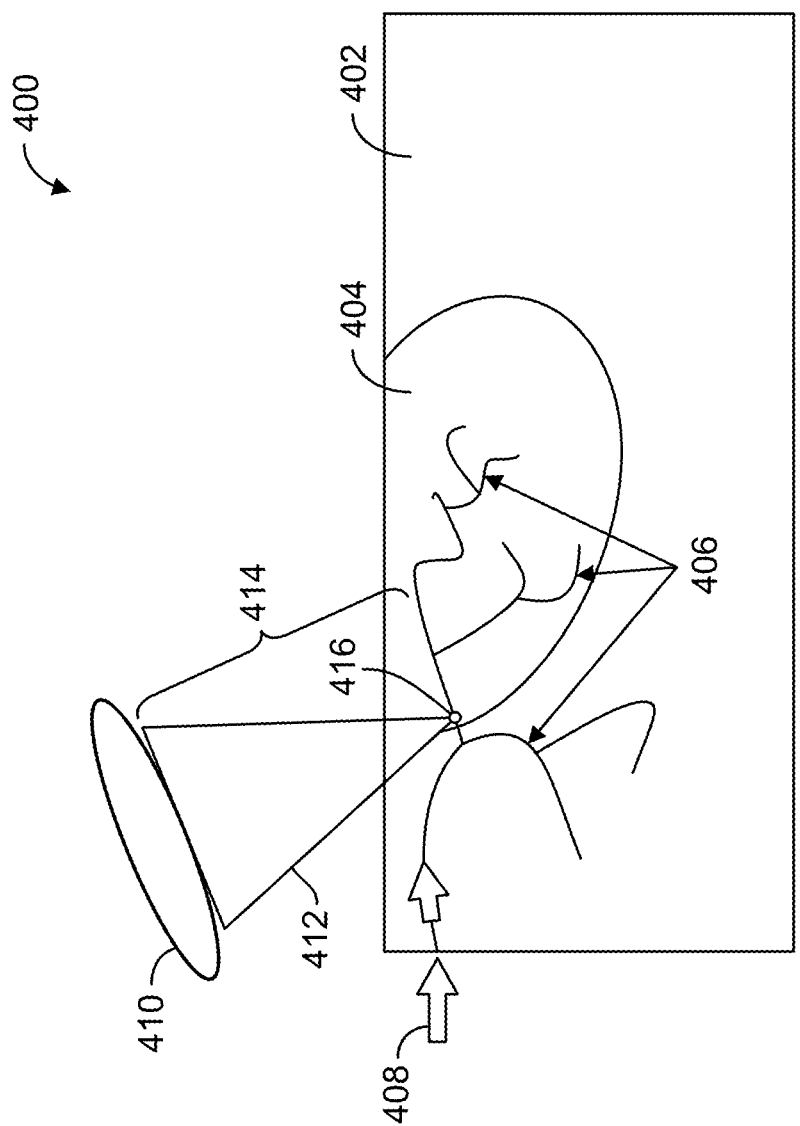
FIG. 4 illustrates a cross-section of a surgical mapping for laser treatment of a skin lesion.

FIG. 4 illustrates a cross-section of a surgical mapping 400 of a surgical site. As illustrated, surgical mapping 400 includes healthy tissue 402 and a lesion 404. In some aspects, surgical mapping 400 can also include a vasculature mapping that identifies one or more blood vessels (e.g., blood vessels 406) that flow through healthy tissue 402 and/or lesion 404. In some cases, surgical mapping 400 can identify blood flow 408 from healthy tissue 402 to lesion 404. Based on the vasculature mapping and blood flow 408, surgical mapping 400 can identify a laser treatment target 416.

In some aspects, laser treatment can be directed toward laser treatment target 416 in order to inhibit blood flow 408 from healthy tissue 402 to lesion 404. In some examples, inhibiting blood flow 408 to lesion 404 can cause necrosis of lesion 404 due to vascular insufficiency. In some embodiments, laser treatment can be administered by using a lens 410 that is configured to focus the laser energy 412 over focal length 414 in order to deliver the laser energy 412 to laser treatment target 416.

Figure 5A:
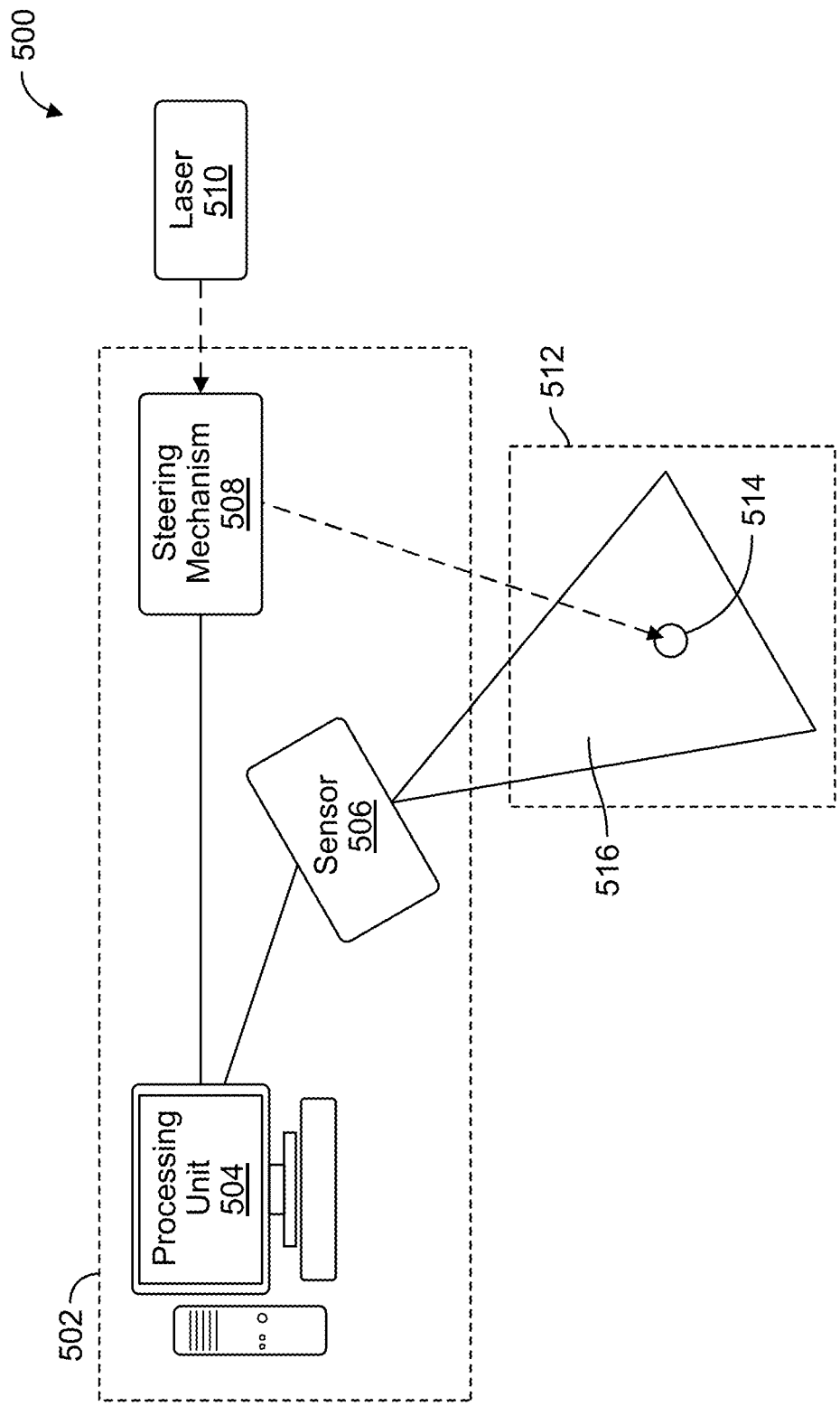
FIG. 5A is a block diagram of a laser treatment system.

FIG. 5A is a block diagram of a laser treatment system 500. In some examples, laser treatment system 500 can include laser controller 502. In some configurations, laser controller 502 can include a processing unit 504, a sensor 506, and a laser steering mechanism 508. In some aspects, processing unit 504 can configure sensor 506 to capture imaging of surgical site 512 (e.g., via a field of view 516 of sensor 506). In some cases, the imaging of surgical site 512 can include a vasculature mapping that can be used to determine a treatment plan (e.g., laser parameters, treatment locations, etc.) for delivering laser energy to surgical site 512.

In some embodiments, imaging of surgical site 512 can be used to identify and/or track laser spot 514. For example, laser controller 502 can be configured to track laser energy provided by laser 510 (e.g., for calibration and/or during treatment). In some aspects, processing unit 504 can configure steering mechanism 508 to deliver laser energy from laser 510 to laser spot 514. In some aspects, laser controller 502 can be configured to operate with an external source (e.g., laser 510). For example, steering mechanism 508 can be coupled to an external laser such as laser 510. In some examples, steering mechanism 508 can include a steerable mirror, a galvanometer, a robotic arm, any other component, and/or any combination thereof for positioning and aiming laser 510 to be incident to laser spot 514. As illustrated, laser 510 is a separate component from laser controller 502 and is not coupled to processing unit 504.

FIG. 5B is a block diagram of a laser treatment system 500. Similar to FIG. 5A, laser treatment system 500 includes laser controller 502. In some aspects, laser controller 502 can include a processing unit 504, a sensor 506, a laser steering mechanism 508 and a laser 510. As illustrated, laser 510 is integrated with laser controller 502 and is coupled to processing unit 504. In some examples, processing unit 504 can configure one or more laser parameters associated with laser 510 for delivering laser energy to laser spot 514 on surgical site 512.

FIG. 6 illustrates an example of a histological evaluation 600 for determining a surface map to perform laser treatment. In some aspects, a histological evaluation 600 can be used to determine a surface map 606 (e.g., tumor map) of residual cancer based on histological assessment following micrographic surgery on periosteum or other biological surfaces (e.g., tumor removal via Mohs micrographic surgery). In some embodiments, histological evaluation 600 can be used to determine a treatment plan for delivering laser energy to treat regions of tissue that are still cancerous but are not further resectable.

In some cases, micrographic surgery can be performed on a surgical site 602 in order to remove targeted tissue 604. In some examples, a histological assessment can be performed on targeted tissue 604 to determine a surface map 606. In some aspects, the surface map 606 can be used to identify target areas (e.g., tumor) for laser treatment. For example, a processor (e.g., processing unit 504) can overlay and/or align surface map 606 with an image of the surgical site 602 for performing laser therapy. In some aspects, a processor can use surface map 606 to determine a treatment plan for performing laser therapy. In some examples, the processor can create a treatment plan to target residual tumor based on surface map 606, the image of the surgical site 602, and/or the overlay of the surgical site and the surface map 606. In some aspects, laser treatment based on histological evaluation 600 can be used to ablate neoplastic foci and/or microscopic foci in cases where further surgery may not be feasible (e.g., bone, such as skull/calvarium, or other biological surfaces), and focused laser therapy can preserve aesthetics, function, and/or reconstructive options.

As noted above, the treatment plan can include one or more laser parameters as well as target locations for delivering laser energy. In some aspects, the processor can direct a surgical system to deliver treatment (e.g., laser energy) to the surgical site 602. In some cases, the techniques described herein can be used to maximize delivery of laser energy to foci of neoplasia and minimizes non-selective damage to surrounding healthy skin, thus maximizing treatment efficacy and minimizing undue adverse effects such as scarring.

Figure 7:
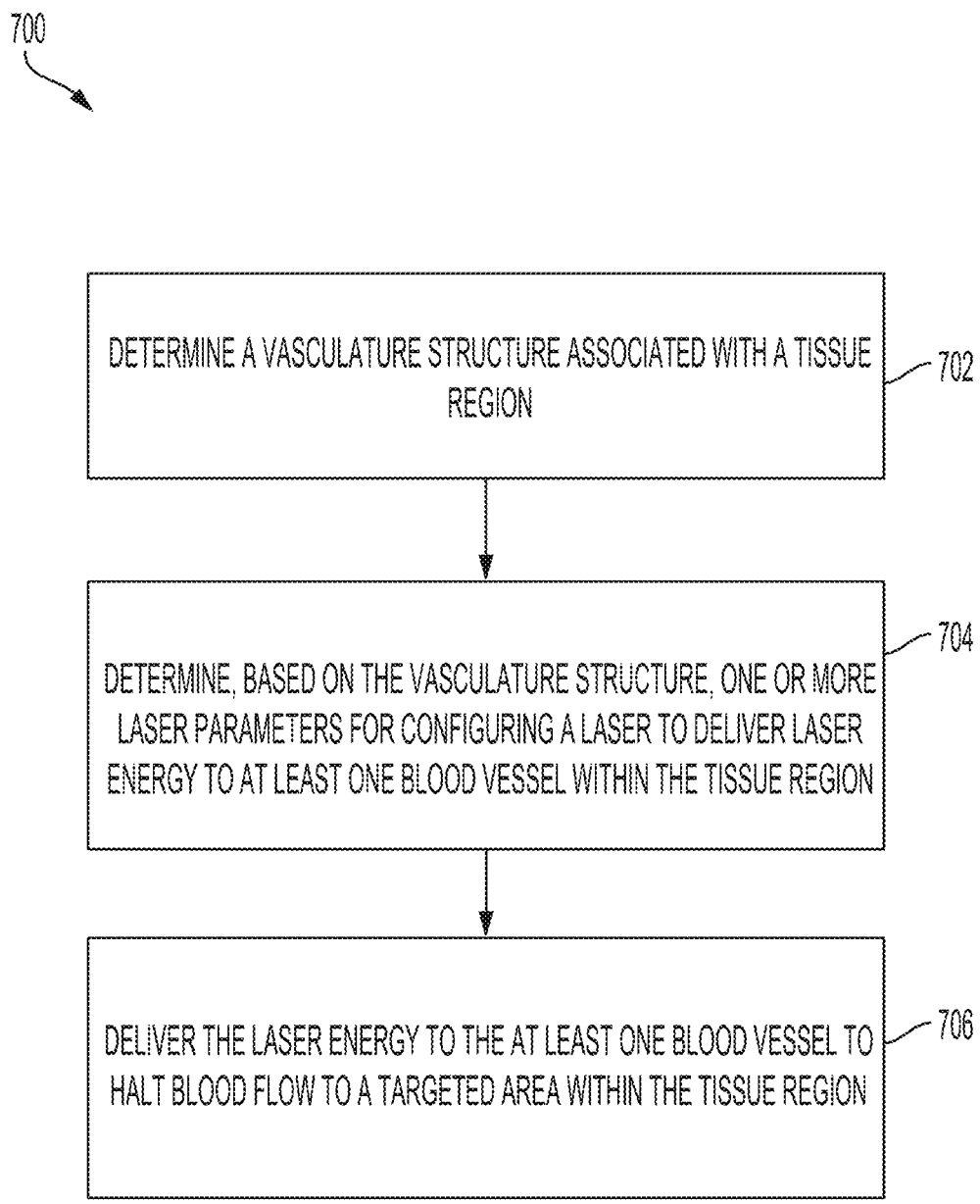
FIG. 7 is a flowchart illustrating another example method for performing laser treatment.

FIG. 7 illustrates an example method 700 for performing imaging-based laser treatment. At block 702, the method 700 includes determining a vasculature structure associated with a tissue region. In some examples, the vasculature structure can be based on as least one biomedical image of the tissue region. In some cases, the at least one biomedical image can correspond to at least one of photoacoustic imaging (PAI), optical coherence tomography (OCT), ultrasound, computed tomography (CT), and magnetic resonance imaging (MRI). In some embodiments, the biomedical image can be obtained using an imaging probe or sensor (e.g., imaging probe 112 or sensor 506). In some aspects, the vasculature structure can be based on a histological evaluation of the tissue region. For example, a histological evaluation 600 can be used to determine a surface map 606 that can be superimposed or overlaid on an image of a surgical site in order to determine a treatment plan.

At block 704, the method 700 includes determining, based on the vasculature structure, one or more laser parameters for configuring a laser to deliver laser energy to at least one blood vessel within the tissue region. In some aspects, the one or more laser parameters can include at least one of a power, a spot size, a wavelength, and a pulse width. For example, a processor (e.g., CPU 104) can implement a treatment planner algorithm (e.g., treatment planner 208) to determine a treatment plan (e.g., treatment plan 214) that can include one or more laser targets (e.g., target 216 and target 218) corresponding to locations in the vasculature structure that target one or more blood vessels. In some cases, the treatment plan (e.g., treatment plan 214) can include or be associated with one or more laser parameters (e.g., laser parameters 222) such as fluence, spot size, wavelength, depth, power, etc.

At block 706, the method 700 includes delivering the laser energy to the at least one blood vessel to halt blood flow to a targeted area within the tissue region. In some examples, the targeted area can correspond to at least one of a basal cell carcinoma (BCC), a squamous cell carcinoma (SCC), and a melanoma in situ (MIS). For example, the targeted area can correspond to lesion 404 located within healthy tissue 402, and the laser energy can be delivered to laser treatment target 416 to halt blood flow 408.

In some aspects, the method 700 can further include determining, based on post-treatment imaging data corresponding to the tissue region, at least one updated laser parameter from the one or more laser parameters. For example, an updated three-dimensional image 206 can be used to modify treatment plan 214 to yield treatment plan 224.

In some embodiments, the method 700 can further include directing a laser-guiding system to position the laser for delivering the laser energy to the at least one blood vessel. For instance, CPU 104 can be coupled to laser guidance 106 and can direct the positioning of laser 110.

Figure 8:
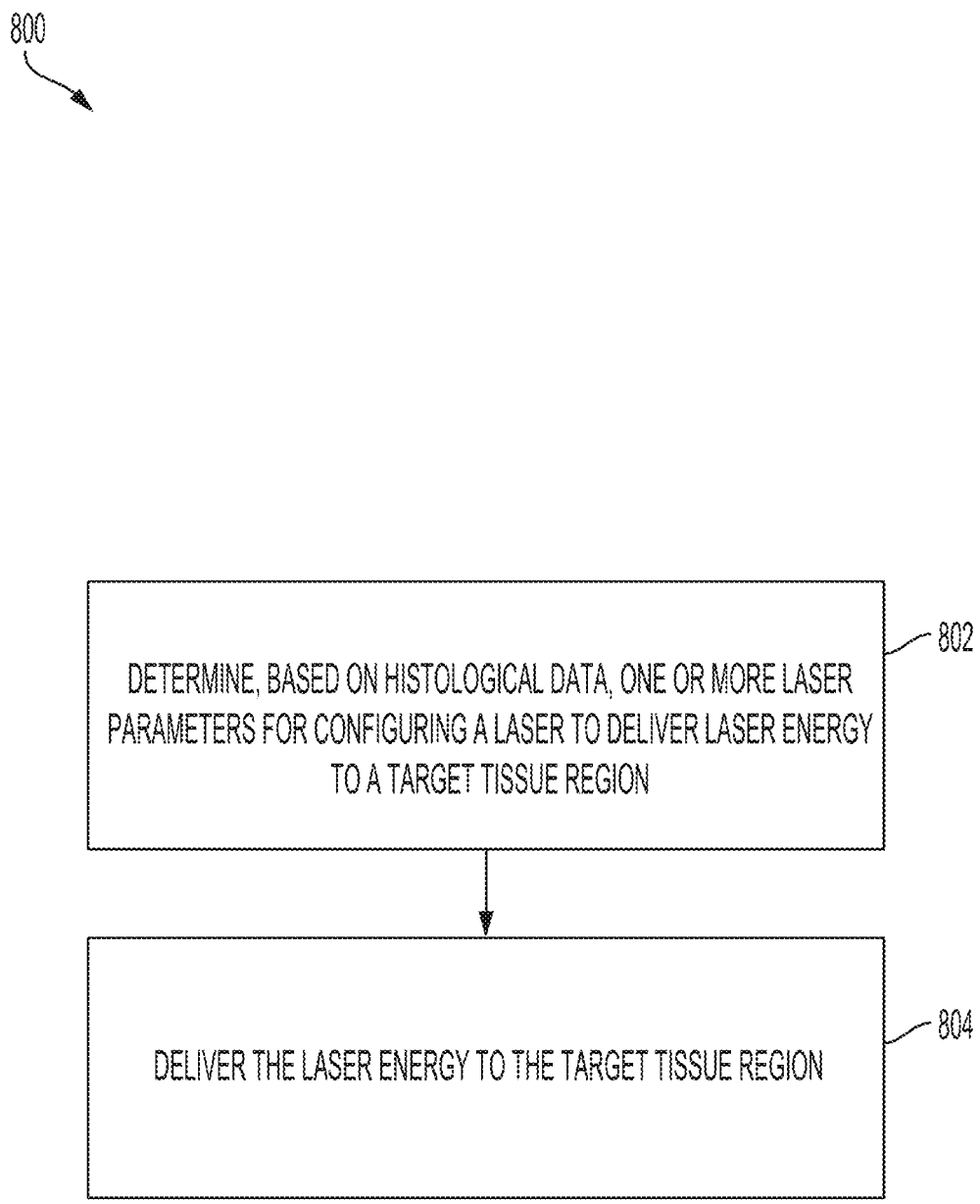
FIG. 8 is a flowchart illustrating another example method for performing laser treatment.

FIG. 8 illustrates an example method 800 for performing imaging-based laser treatment. At block 802, the method 800 includes determining, based on histological data, one or more laser parameters for configuring a laser to deliver laser energy to a target tissue region. In some examples, the histological data can be obtained from tissue (e.g., target tissue 604) that is removed during a surgical procedure such as Mohs micrographic surgery.

In some aspects, the histological data can correspond to a surface map (e.g., surface map 606) that can be used to identify target tissue regions for laser treatment. For example, the surface map can be used to identify tissue regions having cancerous cells that were not removed during a micrographic surgery. In some examples, the surface map can be aligned (e.g., superimposed, overlaid) with an image of the surgical site to facilitate laser treatment of target tissue regions. In some embodiments, the surface map can be used to determine a treatment plan for performing laser treatment.

At block 802, the method 800 includes delivering the laser energy to the target tissue region. In some examples, laser energy can be delivered using a system that can be coupled to an external laser source (e.g., system 500 illustrated in FIG. 5A). In some embodiments, laser energy can be delivered using a system that includes an integrated laser source (e.g., system 500 illustrated in FIG. 5B). In some aspects, a computer-guided laser can provide instruction to an operator for manual aiming of the laser. In some configurations, a computer-guided laser can include a laser-guiding system such as a steerable mirror, galvanometer, robotic arm, or any other component and/or system that can be used to position the laser to be incident on the surgical site at a desired target as identified by the treatment plan.

Figure 9:
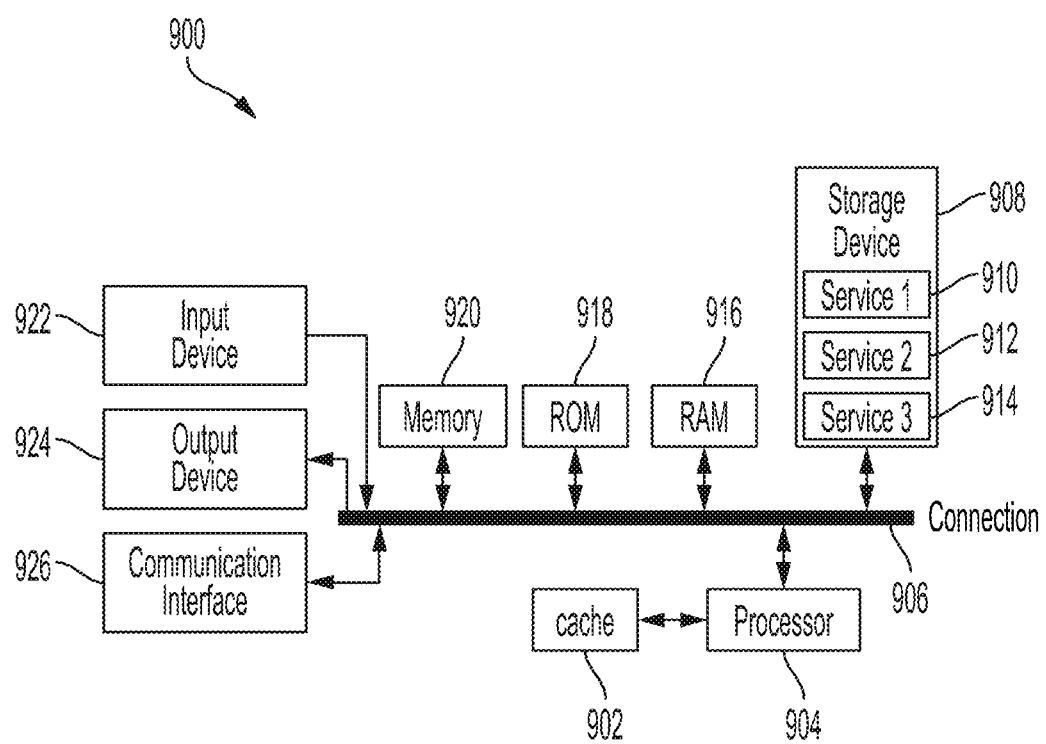
FIG. 9 illustrates an example computing device in accordance with some examples.

FIG. 9 illustrates an example computing system 900 for implementing certain aspects of the present technology. In this example, the components of the system 900 are in electrical communication with each other using a connection 906, such as a bus. The system 900 includes a processing unit (CPU or processor) 904 and a connection 906 that couples various system components including a memory 920, such as read only memory (ROM) 918 and random access memory (RAM) 916, to the processor 904.

The system 900 can include a cache of high-speed memory connected directly with, in close proximity to, or integrated as part of the processor 904. The system 900 can copy data from the memory 920 and/or the storage device 908 to cache 902 for quick access by the processor 904. In this way, the cache can provide a performance boost that avoids processor 904 delays while waiting for data. These and other modules can control or be configured to control the processor 904 to perform various actions. Other memory 920 may be available for use as well. The memory 920 can include multiple different types of memory with different performance characteristics. The processor 904 can include any general purpose processor and a hardware or software service, such as service 1 910, service 2 912, and service 3 914 stored in storage device 908, configured to control the processor 904 as well as a special-purpose processor where software instructions are incorporated into the actual processor design. The processor 904 may be a completely self-contained computing system, containing multiple cores or processors, a bus, memory controller, cache, etc. A multi-core processor may be symmetric or asymmetric.

To enable user interaction with the computing system 900, an input device 922 can represent any number of input mechanisms, such as a microphone for speech, a touch-sensitive screen for gesture or graphical input, keyboard, mouse, motion input, speech and so forth. An output device 924 can also be one or more of a number of output mechanisms known to those of skill in the art. In some instances, multimodal systems can enable a user to provide multiple types of input to communicate with the computing system 900. The communications interface 926 can generally govern and manage the user input and system output. There is no restriction on operating on any particular hardware arrangement and therefore the basic features here may easily be substituted for improved hardware or firmware arrangements as they are developed.

Storage device 908 is a non-volatile memory and can be a hard disk or other types of computer readable media which can store data that are accessible by a computer, such as magnetic cassettes, flash memory cards, solid state memory devices, digital versatile disks, cartridges, random access memories (RAMs) 916, read only memory (ROM) 918, and hybrids thereof.

The storage device 908 can include services 910, 912, 914 for controlling the processor 904. Other hardware or software modules are contemplated. The storage device 908 can be connected to the connection 906. In one aspect, a hardware module that performs a particular function can include the software component stored in a computer-readable medium in connection with the necessary hardware components, such as the processor 904, connection 906, output device 924, and so forth, to carry out the function.

It is to be understood that the systems described herein can be implemented in hardware, software, firmware, or combinations of hardware, software and/or firmware. In some examples, image processing may be implemented using a non-transitory computer readable medium storing computer executable instructions that when executed by one or more processors of a computer cause the computer to perform operations. Computer readable media suitable for implementing the control systems described in this specification include non-transitory computer-readable media, such as disk memory devices, chip memory devices, programmable logic devices, random access memory (RAM), read only memory (ROM), optical read/write memory, cache memory, magnetic read/write memory, flash memory, and application-specific integrated circuits. In addition, a computer readable medium that implements an image processing system described in this specification may be located on a single device or computing platform or may be distributed across multiple devices or computing platforms.

One skilled in the art will readily appreciate that the present disclosure is well adapted to carry out the objects and obtain the ends and advantages mentioned, as well as those inherent therein. The present disclosure described herein are presently representative of preferred embodiments, are exemplary, and are not intended as limitations on the scope of the present disclosure. Changes therein and other uses will occur to those skilled in the art which are encompassed within the spirit of the present disclosure as defined by the scope of the claims.

No admission is made that any reference, including any non-patent or patent document cited in this specification, constitutes prior art. In particular, it will be understood that, unless otherwise stated, reference to any document herein does not constitute an admission that any of these documents forms part of the common general knowledge in the art in the United States or in any other country. Any discussion of the references states what their authors assert, and the applicant reserves the right to challenge the accuracy and pertinence of any of the documents cited herein. All references cited herein are fully incorporated by reference, unless explicitly indicated otherwise. The present disclosure shall control in the event there are any disparities between any definitions and/or description found in the cited references.

What is claimed is:

1. A method of laser treatment, comprising:
   capturing, via at least one imaging probe or sensor, a biomedical image of a tissue region;
   automatically determining, via one or more processors based on the biomedical image, a three-dimensional vasculature structure associated with the tissue region, the three-dimensional vasculature structure including a map of one or more blood vessels that provide blood flow to the tissue region;
   automatically determining, using a trained machine learning (ML) model based on the three-dimensional vasculature structure, one or more laser parameters for configuring a laser to deliver laser energy to at least one blood vessel of the one or more blood vessels within a targeted area of the tissue region, the one or more laser parameters including at least one of power, fluence, depth, spot size, pulse width, or wavelength; and
   delivering, via a processor-guided laser, the laser energy to the at least one blood vessel to halt blood flow to the targeted area within the tissue region.

2. The method of claim 1, width further comprising using the trained ML model to automatically determine a treatment plan for the processor-guided laser including selective photothermolysis or cauterization of the at least one blood vessel.

3. The method of claim 1, wherein the biomedical image is a three-dimensional volumetric image of at least a portion of the image region.

4. The method of claim 3, wherein the biomedical image corresponds to at least one of photoacoustic imaging (PAI), optical coherence tomography (OCT), ultrasound, computed tomography (CT), and magnetic resonance imaging (MRI).

5. The method of claim 1, wherein the vasculature structure is based on a histological evaluation of the tissue region.

6. The method of claim 1, further comprising:
   determining, based on post-treatment imaging data corresponding to the tissue region, at least one updated laser parameter from the one or more laser parameters; and
   using the updated laser parameter to update the trained ML model.

7. The method of claim 6, further comprising:
   updating the trained ML model based on a clinical outcome determined from the post-treatment imaging data.

8. The method of claim 1, wherein the targeted area corresponds to at least one of a basal cell carcinoma (BCC), a squamous cell carcinoma (SCC), and a melanoma in situ (MIS).

9. An apparatus for laser treatment, comprising:
   at least one memory;
   at least one imaging probe or sensor;
   at least one laser; and at least one processor coupled to the at least one memory and the at least one laser, the at least one processor configured to:
- capture, via the at least one imaging probe or sensor, a biomedical image of a tissue region;
- automatically determine, via the at least one processor based on the biomedical image, a three-dimensional vasculature structure associated with the tissue region, the three-dimensional vasculature structure including a map of one or more blood vessels that provide blood flow to the tissue region;
- automatically determine, using a trained machine learning (ML) model based on the three-dimensional vasculature structure, one or more laser parameters for configuring the at least one laser to deliver laser energy to at least one blood vessel of the one or more blood vessels within a targeted area of the tissue region, the one or more laser parameters including at least one of power, fluence, depth, spot size, pulse width, or wavelength; and
- deliver, via the at least one laser controlled by the at least one processor, the laser energy to the at least one blood vessel to halt blood flow to the targeted area within the tissue region.

10. The apparatus of claim 9, wherein the trained ML model is configured to automatically determine a treatment plan for the at least one laser including selective photothermolysis or cauterization of the at least one blood vessel.

11. The apparatus of claim 9, wherein the biomedical image is a three-dimensional volumetric image of at least a portion of the tissue region.

12. The apparatus of claim 11, wherein the biomedical image corresponds to at least one of photoacoustic imaging (PAI), optical coherence tomography (OCT), ultrasound, computed tomography (CT), and magnetic resonance imaging (MRI).

13. The apparatus of claim 9, wherein the vasculature structure is based on a histological evaluation of the tissue region.

14. The apparatus of claim 9, wherein the at least one processor is further configured to:
- determine, based on post-treatment imaging data corresponding to the tissue region, at least one updated laser parameter from the one or more laser parameters; and
- use the updated laser parameter to update the trained ML model.

15. The apparatus of claim 14, wherein the at least one processor is further configured to:
- update the trained ML model based on a clinical outcome determined from the post-treatment imaging data.

16. The apparatus of claim 9, wherein the targeted area corresponds to at least one of a basal cell carcinoma (BCC), a squamous cell carcinoma (SCC), and a melanoma in situ (MIS).

17. A non-transitory computer-readable storage medium having stored thereon instructions which, when executed by one or more processors, cause the one or more processors to:
- capture, via at least one imaging probe or sensor, a biomedical image of a tissue region;
- automatically determine, via the one or more processors based on the biomedical image, a three-dimensional vasculature structure associated with the tissue region, the three-dimensional vasculature structure including a map of one or more blood vessels that provide blood flow to the tissue region;
- automatically determine, using a trained machine learning (ML) model based on the three-dimensional vasculature structure, one or more laser parameters for configuring at least one laser to deliver laser energy to at least one blood vessel of the one or more blood vessels within a targeted area of the tissue region, the one or more laser parameters including at least one of power, fluence, depth, spot size, pulse width, or wavelength; and
- configure the at least one laser to deliver the laser energy, under control of the one or more processors, to the at least one blood vessel to halt blood flow to the targeted area within the tissue region.

18. The non-transitory computer-readable storage medium of claim 17, wherein trained ML model is configured to automatically determine a treatment plan for the at least one laser including selective photothermolysis or cauterization of the at least one blood vessel.

19. The non-transitory computer-readable storage medium of claim 17, comprising instructions which, when executed by the one or more processors, cause the one or more processors to:
- determine, based on post-treatment imaging data corresponding to the tissue region, at least one updated laser parameter from the one or more laser parameters; and
- use the updated laser parameter to update the trained ML model.

20. The non-transitory computer-readable storage medium of claim 19, comprising instructions which, when executed by the one or more processors, cause the one or more processors to:
- update the trained ML model based on a clinical outcome determined from the post-treatment imaging data.

* * * * *

UNITED STATES PATENT AND TRADEMARK OFFICE
CERTIFICATE OF CORRECTION

PATENT NO. : 12,390,273 B2
APPLICATION NO. : 18/088304
DATED : August 19, 2025
INVENTOR(S) : Jigar Patel et al.

It is certified that error appears in the above-identified patent and that said Letters Patent is hereby corrected as shown below:

In the Claims

In Claim 2, Column 12, Line 36, delete "width";

In Claim 18, Column 14, Line 31, after 'wherein' insert --the--.

Signed and Sealed this
Sixteenth Day of September, 2025

Coke Morgan Stewart
*Acting Director of the United States Patent and Trademark Office*